US012080412B2

(12) United States Patent
Schaefer et al.

(10) Patent No.: US 12,080,412 B2
(45) Date of Patent: Sep. 3, 2024

(54) EXTRACORPOREAL BLOOD TREATMENT ALARM DOCKING

(71) Applicant: GAMBRO LUNDIA AB, Lund (SE)

(72) Inventors: Jonas Schaefer, St. Paul, MN (US); John O'Mahony, Maple Grove, MN (US); Thomas Lendway, Vadnais Heights, MN (US)

(73) Assignee: Gambro Lundia AB, Lund (SE)

( * ) Notice: Subject to any disclaimer, the term of this patent is extended or adjusted under 35 U.S.C. 154(b) by 1796 days.

(21) Appl. No.: 15/300,609

(22) PCT Filed: Mar. 26, 2015

(86) PCT No.: PCT/US2015/022634
§ 371 (c)(1),
(2) Date: Sep. 29, 2016

(87) PCT Pub. No.: WO2015/153254
PCT Pub. Date: Oct. 8, 2015

(65) Prior Publication Data
US 2017/0209637 A1 Jul. 27, 2017

Related U.S. Application Data

(60) Provisional application No. 61/972,720, filed on Mar. 31, 2014.

(51) Int. Cl.
*G16H 40/63* (2018.01)
*A61M 1/14* (2006.01)
(Continued)

(52) U.S. Cl.
CPC .............. *G16H 40/63* (2018.01); *A61M 1/14* (2013.01); *A61M 1/34* (2013.01); *A61M 1/36* (2013.01);
(Continued)

(58) Field of Classification Search
CPC .......... G16H 40/63; G06F 19/00; A61M 1/36; A61M 1/14; A61M 1/34; A61M 2205/502;
(Continued)

(56) References Cited

U.S. PATENT DOCUMENTS 5,146,556 A * 9/1992 Hullot ................. G06F 3/04845
715/781
5,305,435 A * 4/1994 Bronson ............... G06F 3/0481
715/775
(Continued)

FOREIGN PATENT DOCUMENTS

EP 2719404 4/2014
WO WO 03/038566 5/2003
(Continued)

OTHER PUBLICATIONS

International Search Report and Written Opinion for Application No. PCT/US2015/022634 dated Jul. 22, 2015 (10 pages).

*Primary Examiner* — Steven B Theriault
(74) *Attorney, Agent, or Firm* — Mueting Raasch Group

(57) ABSTRACT

Extracorporeal blood treatment systems and methods to display information related to an alarm issued during extracorporeal blood treatments. For example, when an alarm is issued, an alarm region may be depicted on a graphical user interface. The alarm region may be configured to be docked into another region of the graphical user interface to, e.g., expose an operations region, etc.

23 Claims, 9 Drawing Sheets

(51) Int. Cl.
  *A61M 1/34*   (2006.01)
  *A61M 1/36*   (2006.01)
(52) U.S. Cl.
  CPC ......... *A61M 1/367* (2013.01); *A61M 2205/18* (2013.01); *A61M 2205/502* (2013.01); *A61M 2205/505* (2013.01); *A61M 2205/52* (2013.01); *A61M 2205/583* (2013.01)
(58) Field of Classification Search
  CPC ........ A61M 2205/583; A61M 2205/18; A61M 2205/505
  See application file for complete search history.

(56) References Cited

U.S. PATENT DOCUMENTS

| | | | | |
|---|---|---|---|---|
| 5,644,737 | A * | 7/1997 | Tuniman | G06F 3/0481 715/810 |
| 5,644,739 | A * | 7/1997 | Moursund | G06F 9/451 715/840 |
| 5,808,610 | A * | 9/1998 | Benson | G06F 3/0481 715/788 |
| 5,819,055 | A * | 10/1998 | MacLean | G06F 3/0481 715/798 |
| 5,825,357 | A * | 10/1998 | Malamud | G06F 3/0481 715/779 |
| 5,883,626 | A * | 3/1999 | Glaser | G06F 40/151 715/788 |
| 5,923,326 | A * | 7/1999 | Bittinger | G06F 3/0481 715/805 |
| 6,072,486 | A * | 6/2000 | Sheldon | G06F 3/0481 715/835 |
| 6,209,011 | B1 * | 3/2001 | Vong | G06F 1/1616 708/112 |
| 6,765,592 | B1 * | 7/2004 | Pletcher | G06F 9/451 715/760 |
| 6,771,292 | B2 * | 8/2004 | Sharp | G06F 3/0486 715/788 |
| 7,523,397 | B2 * | 4/2009 | Cheung | G06F 9/542 715/710 |
| 7,681,134 | B1 * | 3/2010 | Grechishkin | G06F 9/45537 715/740 |
| 7,743,340 | B2 * | 6/2010 | Horvitz | G05B 19/404 715/808 |
| 7,891,625 | B2 | 2/2011 | Chevallet | |
| 8,453,065 | B2 * | 5/2013 | Chaudhrl | G06F 3/0486 715/762 |
| 8,578,290 | B2 * | 11/2013 | Amadio | G06F 3/0481 715/778 |
| 8,607,157 | B2 * | 12/2013 | Shibata | G06F 3/0481 715/803 |
| 8,666,468 | B1 * | 3/2014 | Al-Ali | A61B 5/7275 600/324 |
| 8,875,047 | B2 * | 10/2014 | Beykpour | G06F 3/0481 715/788 |
| 9,104,789 | B2 * | 8/2015 | Gross | G16H 40/67 |
| 9,836,185 | B2 * | 12/2017 | O'Mahony | G06F 3/0482 |
| 10,271,798 | B2 * | 4/2019 | Kassem | A61B 5/743 |
| 10,990,279 | B2 * | 4/2021 | Reynolds | H04L 51/24 |
| 2001/0034614 | A1 * | 10/2001 | Fletcher-Haynes | A61M 1/3496 705/2 |
| 2002/0130904 | A1 * | 9/2002 | Becker | H04L 51/04 715/753 |
| 2003/0058286 | A1 * | 3/2003 | Dando | G06F 9/451 715/853 |
| 2003/0135087 | A1 * | 7/2003 | Hickle | G16H 20/10 600/26 |
| 2003/0154108 | A1 * | 8/2003 | Fletcher-Haynes | G16H 20/40 705/3 |
| 2003/0181815 | A1 * | 9/2003 | Ebner | A61B 5/0002 600/483 |
| 2003/0220897 | A1 * | 11/2003 | Lee | G06F 16/24528 |
| 2004/0034287 | A1 * | 2/2004 | Hickle | A61M 16/01 600/300 |
| 2004/0061716 | A1 * | 4/2004 | Cheung | G06F 9/542 715/710 |
| 2004/0128359 | A1 * | 7/2004 | Horvitz | H04L 67/26 709/207 |
| 2004/0261037 | A1 * | 12/2004 | Ording | G06F 3/0481 715/788 |
| 2005/0229110 | A1 * | 10/2005 | Gegner | G16H 40/63 715/800 |
| 2005/0289478 | A1 * | 12/2005 | Landman | G06F 3/048 715/804 |
| 2007/0044029 | A1 * | 2/2007 | Fisher | G06F 9/451 715/762 |
| 2007/0044032 | A1 * | 2/2007 | Mollitor | H04L 41/22 715/764 |
| 2007/0044035 | A1 * | 2/2007 | Amadio | G06F 3/0481 715/781 |
| 2007/0044039 | A1 * | 2/2007 | Amadio | G06F 9/451 715/847 |
| 2007/0074126 | A1 * | 3/2007 | Fisher | G06F 9/451 715/764 |
| 2007/0266336 | A1 * | 11/2007 | Nojima | G06F 3/0486 715/792 |
| 2008/0126958 | A1 * | 5/2008 | Louie | G06F 3/0481 715/764 |
| 2008/0235352 | A1 * | 9/2008 | Yolleck | H04L 67/34 709/219 |
| 2008/0249377 | A1 * | 10/2008 | Molducci | G16H 40/63 600/301 |
| 2008/0300698 | A1 * | 12/2008 | Havekost | H04L 67/36 700/83 |
| 2009/0005703 | A1 * | 1/2009 | Fasciano | A61B 5/7445 600/561 |
| 2009/0064035 | A1 * | 3/2009 | Shibata | G06F 3/0481 715/803 |
| 2009/0227293 | A1 * | 9/2009 | Yulo | H04W 52/0254 455/566 |
| 2010/0174229 | A1 * | 7/2010 | Hsu | A61M 5/142 604/66 |
| 2010/0265073 | A1 * | 10/2010 | Harper | G08C 19/00 340/573.1 |
| 2010/0281409 | A1 * | 11/2010 | Rainisto | G06F 9/451 715/767 |
| 2011/0119609 | A1 * | 5/2011 | Bhatt | G06F 3/0481 715/765 |
| 2011/0307883 | A1 * | 12/2011 | Hilerio | G06F 8/61 717/176 |
| 2012/0005607 | A1 * | 1/2012 | Tofinetti | G06F 3/0483 715/769 |
| 2012/0054667 | A1 * | 3/2012 | Beykpour | G06F 3/0486 715/781 |
| 2012/0054674 | A1 * | 3/2012 | Beykpour | G06F 3/0481 715/788 |
| 2012/0102400 | A1 * | 4/2012 | Worley | G06F 3/0488 715/702 |
| 2012/0102437 | A1 * | 4/2012 | Worley | G06F 3/04883 715/863 |
| 2012/0138533 | A1 * | 6/2012 | Curtis | A61M 1/16 210/646 |
| 2012/0154264 | A1 * | 6/2012 | Wang | A61M 1/16 345/156 |
| 2012/0198002 | A1 * | 8/2012 | Goulart | H04L 51/36 709/206 |
| 2012/0204191 | A1 * | 8/2012 | Shia | G06Q 10/10 719/318 |
| 2012/0229399 | A1 * | 9/2012 | Kobayashi | G06F 1/1616 345/173 |
| 2013/0113703 | A1 * | 5/2013 | Zheng | G06F 3/038 345/157 |
| 2013/0152007 | A1 * | 6/2013 | Costenaro | G06F 3/0481 715/779 |
| 2014/0102959 | A1 * | 4/2014 | Furuhashi | A61M 1/14 210/85 |
| 2014/0121555 | A1 * | 5/2014 | Scott | A61B 5/24 600/546 |

(56) References Cited

U.S. PATENT DOCUMENTS

| | | | |
|---|---|---|---|
| 2014/0148725 A1* | 5/2014 | Cadwell | A61B 5/296 600/546 |
| 2014/0168053 A1* | 6/2014 | Bergsieker | G06F 3/0481 345/156 |
| 2014/0195865 A1* | 7/2014 | Ikegami | G06F 11/3055 714/57 |
| 2014/0229891 A1* | 8/2014 | O'Byrne | G06F 9/451 715/790 |
| 2015/0012878 A1* | 1/2015 | Chen | G01C 21/26 715/788 |
| 2016/0078747 A1* | 3/2016 | King | G16Z 99/00 340/539.12 |
| 2016/0266742 A1* | 9/2016 | Hussain | G06F 3/04842 |
| 2016/0270740 A1* | 9/2016 | Raisoni | A61B 5/1459 |

FOREIGN PATENT DOCUMENTS

| | | |
|---|---|---|
| WO | WO 2004/069311 | 8/2004 |
| WO | WO 2012/169610 | 12/2012 |
| WO | WO 2014/151669 | 9/2014 |

* cited by examiner

EXTRACORPOREAL BLOOD TREATMENT ALARM DOCKING

CROSS-REFERENCE

This application is a U.S. National Stage Application of International Application No. PCT/US2015/022634, filed Mar. 26, 2015 and published in English on Oct. 8, 2015 as International Publication No. WO 2014/153254 A1, which claims the benefit under 35 U.S.C. 119(e) of U.S. Provisional Application Ser. No. 61/972,720, filed on Mar. 31, 2014, each of which are incorporated herein by reference in their entirety.

BACKGROUND

The disclosure herein relates to extracorporeal blood treatment. More particularly, the disclosure relates to graphical user interfaces configured to display alarm region when alarms are issued during an extracorporeal blood treatment and to allow an operator to dock the alarm region.

Extracorporeal blood treatment may refer to taking blood from a patient, treating the blood outside the patient, and returning the treated blood to the patient. Extracorporeal blood treatment is typically used to extract undesirable matter or molecules from the patient's blood, and/or to add beneficial matter or molecules to the blood. Extracorporeal blood treatment may be used with patients incapable of effectively eliminating matter from their blood, for example, in the case of a patient who is suffering from temporary or permanent kidney failure. These and other patients may, for instance, undergo extracorporeal blood treatment to add to or to eliminate matter from their blood, to maintain an acid-base balance or to eliminate excess body fluids.

In a variety of extracorporeal blood treatments, one or more fluids, or liquids, may be supplied to the extracorporeal blood treatment apparatus for use during the treatments and one or more fluids may be collected as a part of the treatments. Both the supplied and collected fluids may be stored in one or more reservoirs. These reservoirs may, during the course of treatment of a single patient, need to be replaced as they are either emptied (in the case of fluids supplied as a part of the treatment) or are filled to capacity (in the case of fluids collected as a part of the treatment).

During the course of an extracorporeal blood treatment, various alarms may be issued for various issues such as, e.g., problems related to pressure management, patient connections, reservoir volumes, etc. When an alarm is issued, one or more alarm regions, or dialogs, may be displayed on a graphical user interface of an exemplary extracorporeal blood treatment system. The alarm regions, or dialogs, displayed on the graphical user interface may require an operator to perform an action to, e.g., cure or address the alarm before the alarm region, or dialog, may be removed from, or moved within, the graphical user interface. Further, the alarm regions, or dialogs, may obscure one or more regions, portions, or areas of the graphical user interface that an operator may want, or need, to use.

SUMMARY

The present disclosure describes systems and methods that provide graphical user interfaces that include a status region (e.g., for displaying various status information) and an operations region. When an alarm is issued, an alarm region including information relevant to the issued alarm may be displayed, e.g., in the operations region. The alarm region may be docked, e.g., by user interaction, to another region of the graphical user interface such as, e.g., a dock region (e.g., status region).

One extracorporeal blood treatment system may include a display apparatus and a computing apparatus operatively coupled to the display apparatus. The display apparatus may include a graphical user interface, and the graphical user interface may be configured to depict an operations region. The computing apparatus may be configured to display on the graphical user interface an operations region, issue an alarm indicating an issue with an extracorporeal blood treatment being performed, and display, when an alarm is issued, an alarm region in the operations region. The alarm region may include information relevant to the issued alarm. The computing apparatus may be further configured to allow a user to dock the alarm region to another region of the graphical user interface other than the operations region.

One exemplary method for an extracorporeal blood treatment system may include providing a graphical user interface configured to depict an operations region, displaying on the graphical user interface an operations region, issuing an alarm indicating an issue with an extracorporeal blood treatment being performed, and displaying, when an alarm is issued, an alarm region in the operations region. The alarm region may include information relevant to the issued alarm. The exemplary method may further include allowing a user to dock the alarm region to another region of the graphical user interface other than the operations region.

In one or more embodiments, a status region may be further displayed on the graphical user interface, and the alarm region may be docked to the status region (e.g., animation may be used to show the alarm region moving and shrinking as the alarm region is being docked). Further, the operations region may be larger than the status region.

Another exemplary extracorporeal blood treatment system may include a display apparatus and a computing apparatus operatively coupled to the display apparatus. The display apparatus may include a graphical user interface, and the graphical user interface may be configured to depict a dock region. The computing apparatus may be configured to display on the graphical user interface a dock region, issue an alarm indicating an issue with an extracorporeal blood treatment being performed, and display, when an alarm is issued, an alarm region on the graphical user interface. The alarm region may include information relevant to the issued alarm. The computing apparatus may be further configured to allow a user to dock the alarm region to the dock region.

Another exemplary method for an extracorporeal blood treatment system may include providing a graphical user interface configured to depict a dock region, displaying on the graphical user interface a dock region, issuing an alarm indicating an issue with an extracorporeal blood treatment being performed, and displaying, when an alarm is issued, an alarm region on the graphical user interface. The alarm region may include information relevant to the issued alarm. The exemplary method may further include allowing a user to dock the alarm region to the dock region.

In one or more embodiments, the alarm region may further include a dock area configured to be selected by a user to dock the alarm region and/or a mute area configured to be selected by a user to mute the alarm. Further, the alarm region may be further configured to depict an amount of time remaining prior to un-muting the alarm after being muted. Still further, the mute area may be selectable by a user to reset the amount of time remaining prior to un-muting the alarm.

In one or more embodiments, when the alarm region is docked, a user may be allowed to undock the alarm region. Further, the docked alarm region may further include an undock area configured to be selected by a user to undock the alarm region.

In one or more embodiments, the alarm region may further include at least one action area, and when an action area of the at least one action area is selected, an instruction region including information relevant to curing the issued alarm and/or more information relevant to the issued alarm may be displayed on the graphical user interface.

In one or more embodiments, a dock region may be displayed on the graphical user interface. Further, a plurality of alarm regions may be docked and displayed in one or more alarm dock areas of the dock region (e.g., displayed simultaneous, the number of alarms identified, etc.)

In one or more embodiments, the operations region may include a plurality of fluid areas, and each fluid area of the plurality of fluid areas may depict a flow rate. When an alarm is issued, the alarm region may be depicted at least partially over the plurality of fluid areas. Further, for example, a status light, such as light bar may be activated in a mode corresponding to the alarm.

In one or more embodiments, when the alarm region is displayed on the graphical user interface without being docked, a user may be disabled from interacting with any portion the graphical user interface except the alarm region.

In one or more embodiments, when the alarm region is docked, a user may be allowed to interact with the graphical user interface. In one or more embodiments, when the alarm is cured, the alarm region may be removed from the graphical user interface. In one or more embodiments, the size of the alarm region may be scaled based on a severity of the issued alarm. In one or more embodiments, the status region may include therapy information relevant to the extracorporeal blood treatment being performed, and when the alarm region is docked in the status region, the alarm region may include at least a portion of the therapy information of the status region.

The exemplary systems and methods may provide docking of an alarm in order for an operator, or user, to complete a task such as, e.g., to clear an alarm in the same way they would complete the procedure normally (e.g., outside of the alarm dialog, as if the alarm is absent). During an alarm state, there is a period of time in which the operator can troubleshoot and make adjustments as necessary, which may be difficult if an alarm region, or dialog, is obstructing an operator's ability to have full reign of the user interface. Additionally, if an operator docks an alarm region, the exemplary systems and methods may be configured to make sure the operator is aware that the problem that triggered the alarm has not been resolved. More specifically, it should be clear to the operator that the system is still in an alarm state.

Further, in one or more exemplary systems and methods, an audible alarm is associated with many of the alarms. If "mute" is selected in an alarm region, there is an amount of time before the alarm becomes audible again as a reminder that the device is in an alarm state. The operator may need to select the "mute" area again in order to silence the alarm. Docking an alarm region, or dialog, may be associated with muting the alarm (e.g. docking and muting may occur simultaneously; e.g., the alarm may be automatically muted when the alarm is docked), and muting an alarm may also occur while an alarm is docked.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
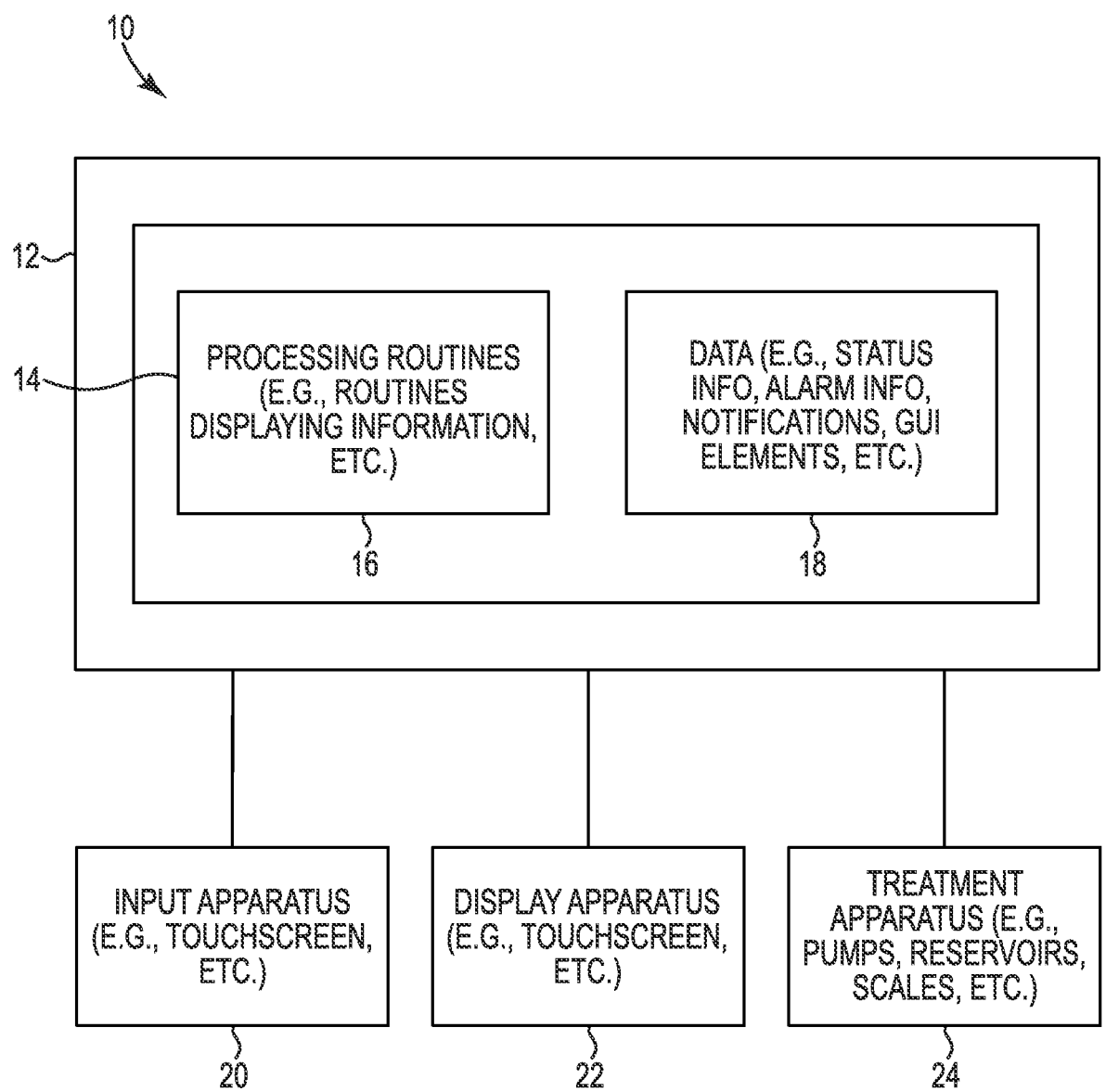
FIG. 1 is a block diagram of an exemplary extracorporeal blood treatment system including input apparatus, display apparatus, and treatment apparatus that may utilize the graphical user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods providing graphical user interfaces for use in extracorporeal blood treatments shall be described with reference to FIGS. 1-8. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary systems and/or methods may include graphically displaying a status region and an operations region (e.g., including, among other things, a fluids region depicting one or more fluid areas having pump elements, flow rate buttons, reservoir elements, etc.) on an exemplary graphical user interface. The status region and the operations region may be described as being separate. For example, the status region and the operations region may not overlap. However, in other embodiments, the status region, the operations region, or any other region may overlap and occupy the same space. In some embodiments, an imaginary or depicted line or lines may separate the status region from the operations region. In some embodiments, the status region may define a boundary, within which the status region lies or is depicted, and the remainder of the display outside of the boundary of the status region may include, or define, the operations region. Further, in some embodiments, the status region and the operations region may be two of many regions depicted on the graphical user interface. Generally, the status region may be smaller than the operations region. In the embodiment depicted in FIGS. 3-8, the status region is located in an upper, left corner of the exemplary graphical user interface and defines a rectangular boundary (e.g., with curved, or rounded, corners) while the operations region defines at least a portion, if not all, of the remainder of the exemplary graphical user interface. Additionally, the exemplary systems and/or methods may include graphically displaying an alarm region on the graphical user interface. In an embodiment described herein, the alarm region may be displayed within the operations region. The alarm region may be docked from one region of the graphical user interface (e.g., the operations region) to a dock region (e.g., the status region) as will be further described herein.

The exemplary systems and methods described herein include docking of alarm regions resulting from issued alarms and undocking of docked alarm regions. Alarms may occur in the exemplary extracorporeal blood treatment systems for multiple reasons, and the reasons may vary in severity (e.g., ranging from low severity to high severity). For example, alarms may be issued for reservoir changes, fluid leaks, electrical issues, abnormal pressures (e.g., pressure management), patient connection, reservoir volumes, other machine malfunctions, etc. Generally, an alarm may be issued for any reason indicating an issue with an extracorporeal blood treatment being performed by an exemplary extracorporeal blood treatment system.

The exemplary issued alarm described herein with respect to FIGS. 3-8 is a reservoir change. During normal operation, a reservoir may need to be changed and, if an operator, or user, has not changed the reservoir (e.g., after a selected time period), an alarm may be issued. The issuance of the alarm may initiate, or trigger, one or more actions such as, e.g., lights flashing on the system, sounds, alarm regions being depicting on the exemplary graphical user interface, messages or alerts sent to remote devices, etc. An exemplary alarm region may include information relevant to the issued alarm such as, e.g., why the alarm issued, how to cure the issued alarm, graphics, or graphical depictions, related to the issued alarm, etc. If an operator determines that the alarm is not imminent or does not need to be immediately addressed, the operator may dock and/or mute the alarm by selecting an area on the alarm region as described in more detail herein with respect to FIGS. 3-8. Additionally, it may be described that the exemplary methods and systems described herein may allow docking or closing of an alarm dialog while still maintaining a visual and audible alarm state in order for an operator to more easily complete a procedure or troubleshoot an alarm.

An exemplary extracorporeal blood treatment system 10 depicted in FIG. 1 may be used to execute, or perform, the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery/collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 that may be employed to carry out exemplary methods and/or processes (e.g., issuing alarms, running a treatment, determining problems with a treatment, exchanging/changing reservoirs, notifying operators/users of problems, displaying status information, etc.) for use in performing extracorporeal blood treatments. For example, the computing apparatus 12 may be configured to display an alarm region on a graphical user interface displayed by the display apparatus 22 to, e.g., indicate that an alarm has been issued (e.g., which will be described further herein with respect to FIGS. 3-8).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, an operator may provide input to the input apparatus 20 to manipulate, or modify, one or more graphical depictions displayed on the display apparatus 22 to select and view various information related to one or more alarms issued during, before, or after any extracorporeal blood treatments.

Further, various devices and apparatus may be operatively coupled to the computing apparatus 12 to be used with the computing apparatus 12 to perform one or more extracorporeal procedures/treatments as well as the functionality, methods, and/or logic described herein. As shown, the system 10 may include input apparatus 20, display apparatus 22, and treatment apparatus 24 operatively coupled to the computing apparatus 12 (e.g., such that the computing apparatus 12 may be configured to use information, or data, from the apparatus 20, 22, 24 and provide information, or data, to the apparatus 20, 22, 24). The input apparatus 20 may include any apparatus capable of providing input to the computing apparatus 12 to perform the functionality, methods, and/or logic described herein.

For example, the input apparatus 20 may include a touchscreen (e.g., capacitive touchscreen, a resistive touchscreen, a multi-touch touchscreen, etc.), a mouse, a keyboard, a trackball, etc. A touchscreen may overlay the display apparatus 22 such that, e.g., an operator may use the touchscreen to interact (e.g., by touch) with a graphical user interface displayed on the display apparatus 22. For example, the input apparatus 20 may allow an operator to interact with a graphical user interface including an alarm region containing, or depicting, information related to the issued alarm to, e.g., clear the alarm, dock the alarm, mute the alarm, postpone the alarm, provide/display more information regarding the alarm, etc. when used in conjunction with the display apparatus 22 (e.g., displaying the graphical user interface).

The display apparatus 22 may include any apparatus capable of displaying information to an operator, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. As described further herein, the display apparatus 22 may be configured to display a graphical user interface that includes one or more regions such as an operations region, a status region, one or more alarms regions as well as various other regions and areas.

For example, the graphical user interface displayed by the display apparatus 22 may include, or display, an operations region that may include multiple items related to the extracorporeal blood treatment such as, e.g., one or more fluid areas, each fluid area corresponding to a different fluid used in an extracorporeal blood treatment. Further, each of these fluid areas may be used by an operator to view status information corresponding to a fluid such as flow rate, amount of fluid within a reservoir, an amount of time left before a reservoir change, etc.

As used herein, a "region" of a graphical user interface may be defined as a portion of the graphical user interface within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface may be defined as a portion of the graphical user interface located with a region that is smaller than the region the area is located within.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, alarm data, fluid data, flow rates, fluid volumes, notifications, pressures, pressure limits, blood flow, blood flow limits, fluid removal rates, fluid removal limits, target blood temperatures, blood temperature limits, heuristics indicative of malfunction, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and, when executed by a processor, is operable to perform operations such as the methods, processes, and/or functionality described herein.

Likewise, the system 10 may be configured at a remote site (e.g., an application server) that allows access by one or more operators via a remote computer apparatus (e.g., via a web browser), and allows an operator to employ the functionality according to the present disclosure (e.g., user accesses a graphical user interface associated with one or more programs to process data).

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by an operator.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The treatment apparatus 24 may include any apparatus used by an exemplary extracorporeal blood treatment system capable of performing extracorporeal blood treatments, such as, e.g., pumps, reservoirs, scales, treatment sets, filters, pressure sensors, etc. For example, the treatment apparatus 24 may include one or more elements, or components, of the extracorporeal blood treatment system 100 described herein with reference to FIG. 2.

The exemplary systems, and exemplary methods performed, or used, by such exemplary systems, described herein may be generally referred to as dialysis systems. The general term "dialysis" as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) shall be described herein with reference to the exemplary extracorporeal blood treatment system of FIG. 2, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

Figure 2:
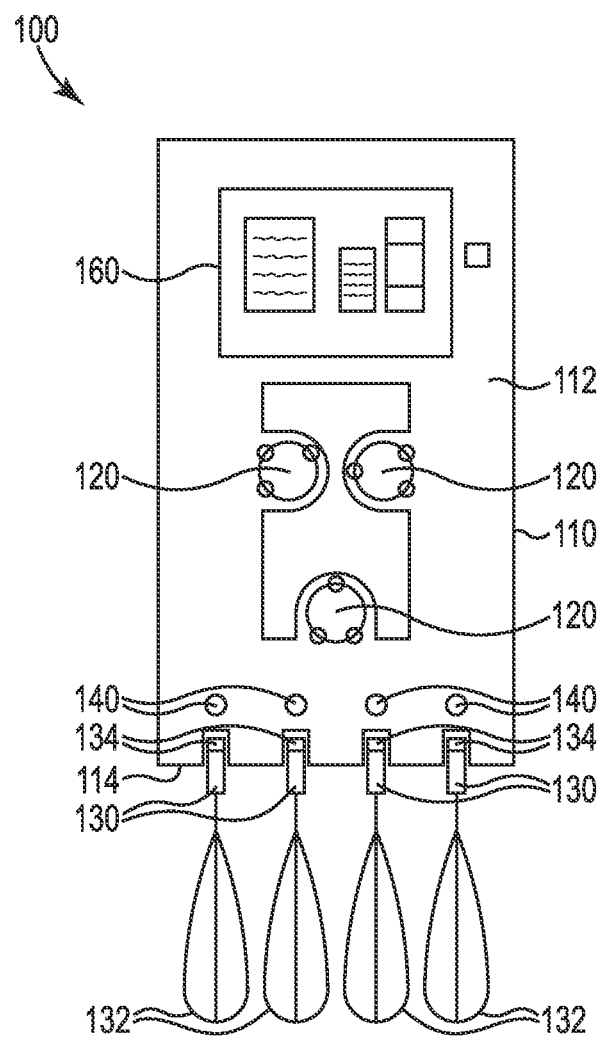
FIG. 2 is an illustration of an exemplary extracorporeal blood treatment system that may include graphical user interfaces as described herein.

Referring to FIG. 2, one illustrative embodiment of an extracorporeal blood treatment system, or apparatus, 100 is depicted. The system 100 includes a housing 110 having a front face 112. The system further includes one or more pumps 120 used to move liquids through the apparatus as part of a treatment process. Although the pumps 120 are depicted in the form of peristaltic pumps, the pumps used in the extracorporeal blood treatment system described herein may be provided in a variety of alternative forms, e.g., piston pumps, pumps for use with syringes, diaphragm pumps, etc.

The extracorporeal blood treatment system 100 also includes, in one or more embodiments, a display 160 used to convey information to an operator or user. The display 160 may also serve as an input device if, e.g., the display 160 is in the form of a touchscreen. Also, although the display 160 is depicted as being located in the housing 110, in one or more alternate embodiments, the display 160 may be separate from the housing 110 of the extracorporeal blood treatment system 100. For example, the display 160 may be movably (e.g., swivel, tilt, etc.) attached, or coupled, to a top end of the housing 110.

The extracorporeal blood treatment system 100 also includes reservoir scales 130, each of which is configured to hold and weigh a reservoir 132. The reservoir scales 130 are positioned below a bottom end 114 of the housing 110, at least in part because the reservoirs 132 are typically attached to and hang from the reservoir scales 130. Although the depicted embodiment of extracorporeal blood treatment system 100 includes four reservoir scales 130 and associated reservoirs 132, alternative embodiments of an extracorporeal blood treatment apparatus as described herein may include one or more reservoir scales 130 and associated reservoirs 132 such as, e.g., as few as two reservoirs scales 130 and associated reservoirs 132, four or more reservoirs scales 130 and associated reservoirs 132, etc.

In the embodiment shown, the reservoirs 132 may be in the form of, e.g., flexible polymeric bags configured to hold liquids. Reservoirs 132, however, used in connection with the exemplary extracorporeal blood treatment systems described herein may take any suitable form in which liquids can be stored and weighed by any scale or weighing apparatus (e.g., such as reservoir scales 130), e.g., bottles, tanks, cartons, syringes, jugs, etc.

The extracorporeal blood treatment system 100 depicted in FIG. 2 may also include passive color indicators 134 on each of the reservoir scales 130. The passive color indicators 134 may be used as a designation of the contents of each of the reservoirs 132 attached to the reservoir scale 130. For example, if one of the reservoirs 132 is connected to the extracorporeal blood treatment system 100 to collect waste fluid from, e.g., a dialysis filter, the passive color indicator 134 associated with the reservoir scale 130 holding the waste reservoir 132 may have a selected color that is different than, e.g., a reservoir scale 130 holding a reservoir 132 that is used to supply dialysate liquid within the same extracorporeal blood treatment system 100. The passive color indicators 134 used in connection with an extracorporeal blood treatment system as described herein may be in the form of patches, stickers, paint, or any other suitable technique of displaying a color to an operator of the extracorporeal blood treatment system that does not involve emitting light. Although the passive color indicators 134 are depicted as being located on the reservoir scales 130, the passive color indicators 134 may, in one or more embodiments, be located on the housing 110, while in one or more other embodiments passive color indicators may be located on both the reservoir scales 130 and the housing 110.

A plurality of reservoir status lights 140 are also depicted in connection with the extracorporeal blood treatment system 100 of FIG. 2 and may be used to monitor the status of the reservoirs 132 attached to the reservoir scales 130 associated with the reservoir status lights 140. In one or more embodiments, the reservoir status lights 140 are located below the one or more pumps 120 and the display 160 of the extracorporeal blood treatment system 100. Because, in one or more embodiments, the reservoirs 132 hang from the reservoir scales 130, the reservoir status lights 140 may be described as being located below the one or more pumps 120 and above the reservoirs 132 attached to the reservoir scales 130 of the extracorporeal blood treatment system 100. Further, although the reservoir status lights 140 are depicted as being located on the front face 112 of the housing 110, the reservoir status lights 140 may, in one or more alternative embodiments, be provided on the reservoir scales 130 and/or on other surfaces of the extracorporeal blood treatment system 100. In such an embodiment, one or more passive color indicators 134 associated with each of the reservoir scales 130 may be located on the housing 110 and/or on the reservoir scales 130. Further, for example, one or more other status lights (e.g., alarm lights) may be located at the upper portion of the housing 110 (e.g., on the top of the system), such as, in the form of a light bar 131. For example, such status lights may be activated when an alarm is present (e.g., a colored bar may be activated, a moving light along the bar may be presented, a blinking bar may be presented, etc.).

Each of the reservoir status lights 140 may be associated with only one reservoir scale 130 of the extracorporeal blood treatment system 100. For example, a first reservoir status light 140 may be associated with a first reservoir scale 130, while a second reservoir status light 140 may be associated with a second reservoir scale 130. Although the depicted extracorporeal blood treatment system 100 includes only one reservoir status light 140 associated with each reservoir scale 130, in one or more alternative embodiments, two or more reservoir status lights 140 may be associated with one reservoir scale 130.

The display 160 may be used to monitor the operation of the extracorporeal blood treatment system 100 as well as the status of any reservoirs 132 attached to the reservoir scales 301 as described herein with reference to FIGS. 3-8. In the extracorporeal blood treatment system 100 described herein, the reservoir status lights 140 can, in one or more embodiments, be used to provide an indication of the status of a reservoir 132 attached to the reservoir scale 130 that is associated with a reservoir status light 140. For example, a reservoir status light 140 associated with a selected reservoir scale 130 is located closer to the selected reservoir scale 130 than any other reservoir scale 130 provided in the extracorporeal blood treatment apparatus. In the case of a first reservoir status light 140 associated with a first reservoir scale 130 and a second reservoir status light 140 associated with a second reservoir scale 130, the first reservoir status light 140 emits light from a location that is closer to the first reservoir scale 130 than the second reservoir scale 130.

In one or more embodiments, the reservoir status light 140 associated with a reservoir scale 130 may provide an indication that a reservoir 132 attached to the reservoir scale 130 has passed a selected weight limit as a part of monitoring the status of the reservoirs. That selected weight limit may, in the case of a reservoir 132 used to collect liquids from the extracorporeal blood treatment apparatus, be an upper limit such that passing (e.g., reaching and/or exceeding) the selected weight limit is an indication that the reservoir 132 is reaching or has reached its loading capacity and may need to be replaced with a reservoir 132 having more capacity to collect liquid. In the case of a reservoir 132 used to supply liquids to the extracorporeal blood treatment apparatus, the selected weight limit may be a lower limit such that passing (e.g., reaching and/or falling below) the selected weight limit is an indication that the reservoir 132 is reaching or has reached a level at which the reservoir 132 may need to be replaced with a fresh reservoir 132 containing additional liquid to be supplied to the extracorporeal blood treatment system 100.

The reservoir status lights 140 may be used in conjunction with alarms issued by the exemplary extracorporeal blood treatment system 100. For example, when an alarm is issued by the system 100 relating to a reservoir 132 (e.g., a reservoir 132 that may require, or be nearing, replacement, a reservoir 132 that may need to be adjusted, a reservoir 132 that may need any other operator intervention, etc.), an alarm region may be depicted on an exemplary graphical user interface displayed on the display 160 and the reservoir status light 140 corresponding to the reservoir 132 that may have triggered the alarm may provide an indication (e.g., the status light may illuminate, or light up). Additionally, the alarm region depicted on a graphical user interface on the display 160 may use an identifier such as, e.g., a color, a number, and/or a description, that corresponds to the reservoir 132 that triggered the alarm and/or reservoir status light 140 and/or passive color indicator 134 of the reservoir 132 that triggered the alarm. For example, an alarm may be issued for a reservoir 132 that needs to be replaced, and the alarm region depicted on an exemplary graphical user interface may include a colored icon corresponding to the reservoir status light 140 and/or passive color indicator 134 of the reservoir needing replacement. In at least one embodiment, the alarm region may include a number corresponding to the reservoir 132 needing replacement.

As shown in FIG. 1 and as related to FIG. 2, the treatment apparatus 24 may be operatively coupled, or connected, to the computing apparatus 12. Among the treatment apparatus 24 operably coupled to the computing apparatus 12 are the pumps 120 and reservoir scales 130 as shown in FIG. 2. Also, among the treatment apparatus 24 operably coupled to the computing apparatus 12 are the reservoir status lights 140.

The computing apparatus 12 may, in one or more embodiments, be configured to receive a weight signal from each reservoir scale 130, with the weight signal from each reservoir scale 130 being indicative of the weight of a reservoir 132 attached to the reservoir scale 130. The computing apparatus 12 may further be configured to make a determination that the reservoir 132 attached to the reservoir scale 130 from which the weight signal has been received has passed a selected weight limit at least partially based on the weight signal received from the reservoir scale 130. As discussed herein, the selected weight limit may be an upper limit or a lower limit depending on whether the reservoir is used to supply liquid or collect liquid from the extracorporeal blood treatment system 100. If the computing apparatus 12 makes a determination that a reservoir 132 associated with a reservoir scale 130 has passed the selected weight limit, the computing apparatus 12 may further be configured to change a mode of light emitted by the reservoir status light 140 associated with the reservoir scale 130 (e.g. varying the intensity of the light, changing the brightness of the light, turning the light on and off such that it blinks, blinking the light at one or more different rates, changing the color of the light, etc.) and/or to display various status information such as notifications on the graphical user interface. Further, for example, the computing apparatus may be configured to control one or more other status lights, such as, the light bar 131. For example, similar changes in the mode of light emitted by the status bar 131 may be controlled by the computing apparatus (e.g., different light colors for different alarm states).

The reservoir scales used to hold and weigh reservoirs used in the extracorporeal blood treatment apparatus described herein may take any number of a variety of different forms. Examples of some potentially suitable reservoir scales and associated structure may be found in International Publication WO 2004/069311 and U.S. Pat. No. 7,891,625, as well as the reservoir scales and hangers used in some commercially available hemodialysis machines (e.g., PRISMAFLEX machines available from Gambro Lundia AB, etc.).

Screenshots depicting exemplary graphical user interfaces for use in displaying information related to extracorporeal blood treatments and providing functionality (e.g., docking alarm regions) to an operator for use in performing the extracorporeal blood treatments are depicted in FIGS. 3-8. Such exemplary graphical user interfaces may be depicted by the display apparatus 22 of the system 10 described herein with reference to FIG. 1 and/or the display 160 of the system 100 of FIG. 2. Additionally, the graphical user interfaces described herein may be depicted on a touch-screen, and in such configuration, the input apparatus would also be the touchscreen.

Figure 3:
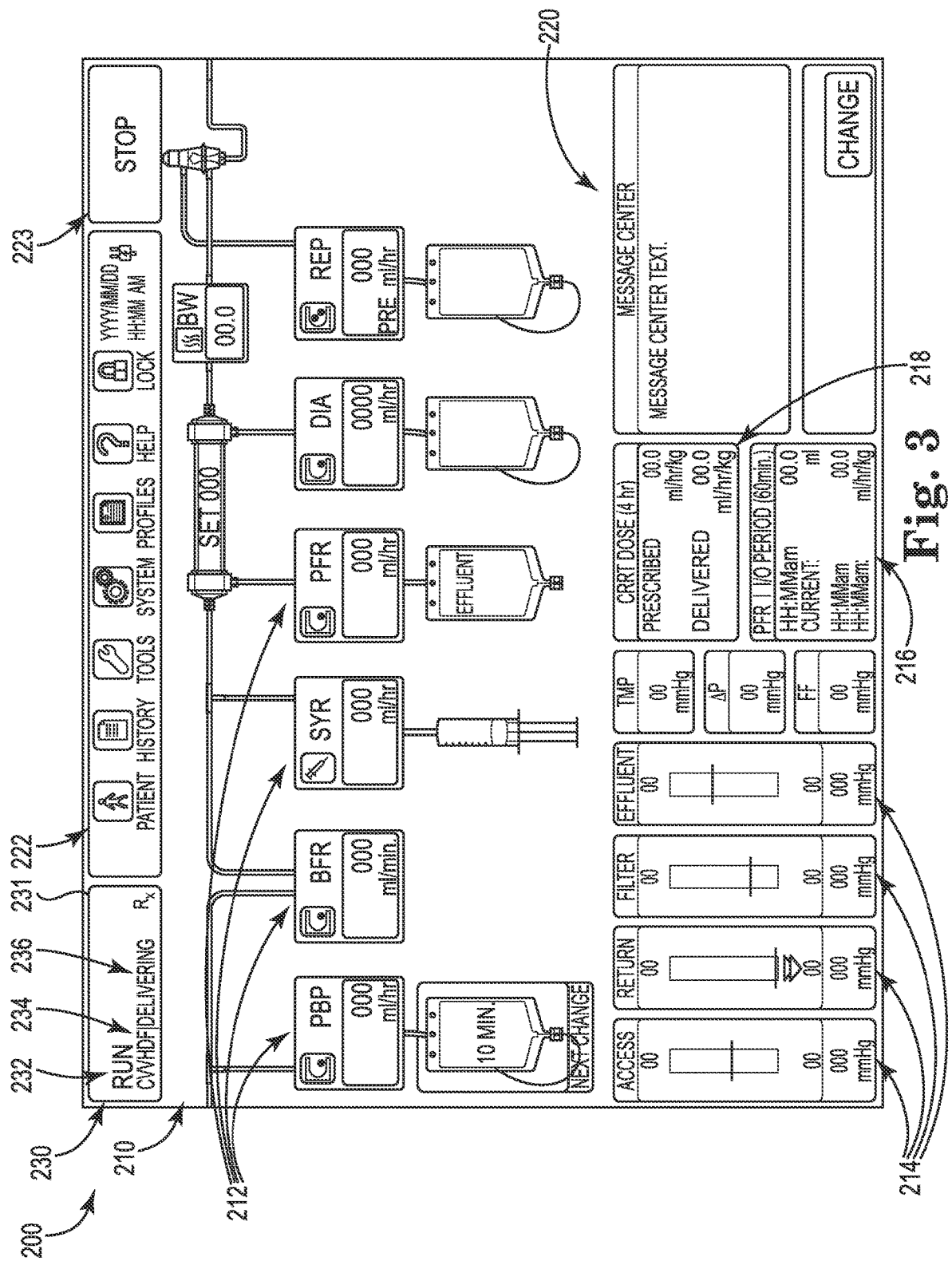
FIGS. 3-8 are screenshots of exemplary graphical user interfaces related to alarms for use in extracorporeal blood treatment systems, for example, such as shown generally in FIGS. 1-2.

An exemplary graphical user interface 200 is depicted in FIG. 3 that may be generally used during and/or for the execution of an extracorporeal blood treatment. The graphical user interface 200 may include, among other regions, an operations region 210 that may include multiple items related to the extracorporeal blood treatment such as, e.g., one or more fluid areas 212, one or more pressure display areas 214, input/output time period area 216, dosage information area 218, message center area 220, etc. Each fluid area 212 may correspond to a different fluid used in an extracorporeal blood treatment. Exemplary fluid areas may be described in PCT Patent Application No. PCT/US2014/026215 filed on Mar. 14, 2014 and entitled "Extracorporeal Blood Treatment Fluids Interface," which is incorporated herein by reference in its entirety.

The graphical user interface 200 may also include a status region 230 configured to display therapy information such as, e.g., machine status 232, therapy type 234, and therapy status 236. As shown, the status region 230 is located in the upper left corner of the graphical user interface 200. The status region 230 may be located anywhere on the graphical user interface 200 including overlapping other regions, such as the operations region 210. In at least one embodiment, the status region 230 may be described as including a boundary 231 that defines the outside of the status region 230 and the operations region 210 may define the remainder of the graphical user interface region 200.

The graphical user interface 200 may also include additional regions such as the tool bar region 222 configured to provide one or more selectable areas for accessing various settings and/or information for the exemplary extracorporeal blood treatment system. As shown, the tool bar region 222 includes a "Patient" area, "History" area, "Tools" area, "System" area, "Profiles" area, "Help" area, and "Lock" area, each of which may be selectable by an operator (e.g., by touching, clicking with a mouse, etc.) to access various other areas and/or region of the graphical user interface 200. The graphical user interface 200 may also include a Stop/Cancel region 223 configured to be selected by an operator to start, stop, or pause, an extracorporeal blood treatment system being performed by the exemplary extracorporeal blood treatment system. As shown, the Stop/Cancel region 223 defines a "Stop" or "Cancel" action, which may stop or cancel an ongoing blood treatment and/or stop or cancel any other operation of the exemplary extracorporeal blood treatment system 10.

A operator may use input apparatus 20 of the exemplary extracorporeal blood treatment system 10 described herein with reference to FIG. 1 to select the regions and areas of the graphical user interface 200. For example, the input apparatus 20 may be a touch screen that corresponds to the graphical user interface 200. As used herein, when an operator "selects" a region or area of the graphical user interface, it is to be understood that selecting the region or area may be conducted in many different ways using many different types of input apparatus. For example, when the input apparatus is a touch screen, an operator may select a region or area by "touching" the region or area with their finger or using a pointing device such as a stylus. Further, for example, when the input apparatus is a mouse or similar pointing device, an operator may select a region or area by locating an arrow or cursor over the desired region or area "clicking" the region or area. Still further, for example, when the input apparatus is a series of buttons and/or knobs, an operator may select a region or area by using the buttons and/or knobs to navigate to the region or area and selecting it by depressing a button and/or knob.

As described herein, an exemplary extracorporeal blood treatment system may issue an alarm for multiple reasons such as e.g., reservoir changes, reservoir malfunctions, abnormal pressures, leaks, pressure management, patient connections, reservoir volumes, etc. When an alarm is issued, numerous actions may be performed, or executed, by the exemplary extracorporeal blood treatment system. For example, an exemplary extracorporeal blood treatment system may include output apparatus such as lights, speakers, etc. that may be configured to notify (e.g., using lights, sounds, light bars, etc.) an operator that an alarm has been issued. Further, as described herein, an alarm region may be displayed on an exemplary graphical user interface 200 to notify an operator that an alarm has been issued.

Figure 4:
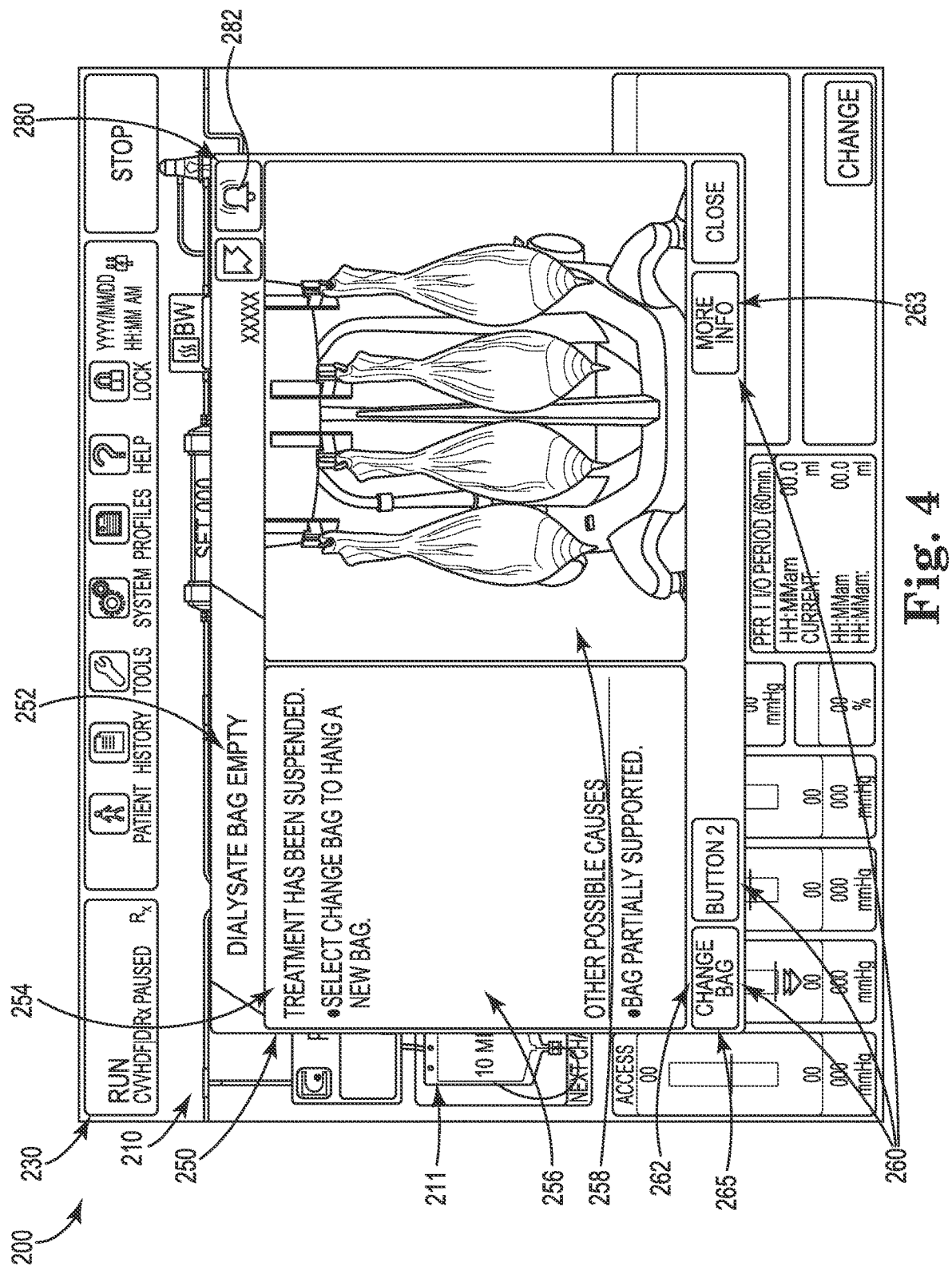

An exemplary alarm region 250 is depicted on the graphical user interface 200 in FIG. 4. The alarm region 250 may be configured to display information related to the issued alarm and to provide selectable actions for an operator to select that are relevant to the issued alarm. For example, the alarm region 250 may provide functionality for an operator to gather information related to the issued alarm and execute one or more processes or steps to cure the issued alarm. After an alarm has been cured (e.g., addressed or fixed by an operator, etc.), the alarm region 250 may be removed from the graphical user interface 200 (e.g., the alarm region 250 may not be depicted any longer, the alarm region 250 may disappear, etc.).

As shown, the alarm region 250 is displayed in (e.g., on, above, within, etc.) the operations region 210. In at least one embodiment, the alarm region 250 may be described as being a "pop-over" window (e.g., a graphical element that is located over the remainder of the graphical user interface 200). Further, the alarm region 250 may flash or depict any attention "grabbing" graphical animation.

The remainder 211 of the operations regions 210 that is not obscured or blocked from view by the alarm region 250 may be "greyed out" (e.g., the graphics in the operations region 210 may be "greyed" or darkened, the graphics in the operations region 210 may have "low light," etc.), which may indicate that the functionality provided within the operations region 210 may be disabled while the alarm region 250 is displayed in the operations region 210. Although the operations region 210 may be "greyed out" and not functional (e.g., not selectable by an operator, not usable to perform actions by an operator, etc.), the values (e.g., fluid reservoir levels, pressures, temperatures, and/or any other information displayed in the operations region 210) depicted may still be updated based on the operations of the extracorporeal blood treatment system. Further, although the exemplary embodiment described herein "greys out" the operations regions 210 while the alarm region 250 is depicted, other embodiments may use some other type of graphical indication (e.g., blurring, etc.) that the operations regions 210 is non-functional. Still further, in other embodiments, the operations 210 may still be functional when the alarm region 250 is displayed thereon.

Although the alarm region 250 is depicted in FIG. 4 as being a particular size and shape, the size and shape of the alarm region 250 may change, or vary, depending on severity of the issued alarm. For example, a more serious alarm (e.g., an alarm requiring more immediate attention) may be larger while a less serious alarm (e.g., an alarm requiring less immediate attention) may be smaller. Additionally, although the figures are in black and white, the color of the alarm region 250 may change depending on severity of the issued alarm.

The alarm region 250 includes one or more areas, some user selectable and others not user selectable. For example, the alarm region 250 may include a title area 252 that displays the title of the alarm in alphanumeric characters and/or a brief description of the issued alarm. An operator may view, or look at, the title area 252 and read the information contained therein to quickly ascertain the type of the issued alarm. The title area 252 may also be color-coded depending on the severity of the alarm. For example, some alarms may be more serious or may need more immediate attention than others, and thus, the title area 252 of some alarms may be a particular, or preselected, color (e.g., red) to indicate a more severe alarm while other alarms may be another particular, or preselected, color (e.g., yellow) to indicate a less severe alarm. Further, for example, a status light, such as light bar 131 may be activated in a mode corresponding to the displayed alarm. For example, the status light 131 may be color coded like the displayed alarm, the status light may be activated to flash at different speeds depending on the displayed alarm, may be activated so that light moves along the light bar more rapidly depending on the displayed alarm, etc.

The alarm region 250 may further include an information area 254 that provides textual and/or graphical information with respect to the issued alarm. For example, as shown, the information area 254 includes text 256 that may describe the issued alarm in more detail and a graphic 258 that may graphically depict a portion of the exemplary extracorporeal blood treatment system proximate the event that triggered the alarm, a portion of the exemplary extracorporeal blood treatment system where the issued alarm may be addressed or cured, etc. Further, the information depicted in the information area 254 may be scrollable or movable to depict more information.

The exemplary issued alarm indicated by the alarm region 250 of FIG. 4 is a reservoir change. As such, a title area 252 includes the text "Reservoir Change," the text 256 (e.g., one or more strings of alphanumeric characters) of the information area 254 includes text related to the reservoir change including but not limited to one or more steps, instructions, or processes, to change the reservoir, tips and/or reminders regarding the reservoir, etc., and the graphic 258 of the information area 254 depicts a lower portion or region of the exemplary extracorporeal blood treatment system including the reservoirs and reservoir scales.

The alarm region 250 may further include one or more (e.g., at least one) action areas 260 that may be selectable by an operator to perform, execute, or initiate, one or more actions or operations. Each of the actions areas 260 may be described as being a selectable button, and each of the action areas 260 may include a text description 262 of the action area 260.

Figure 8:
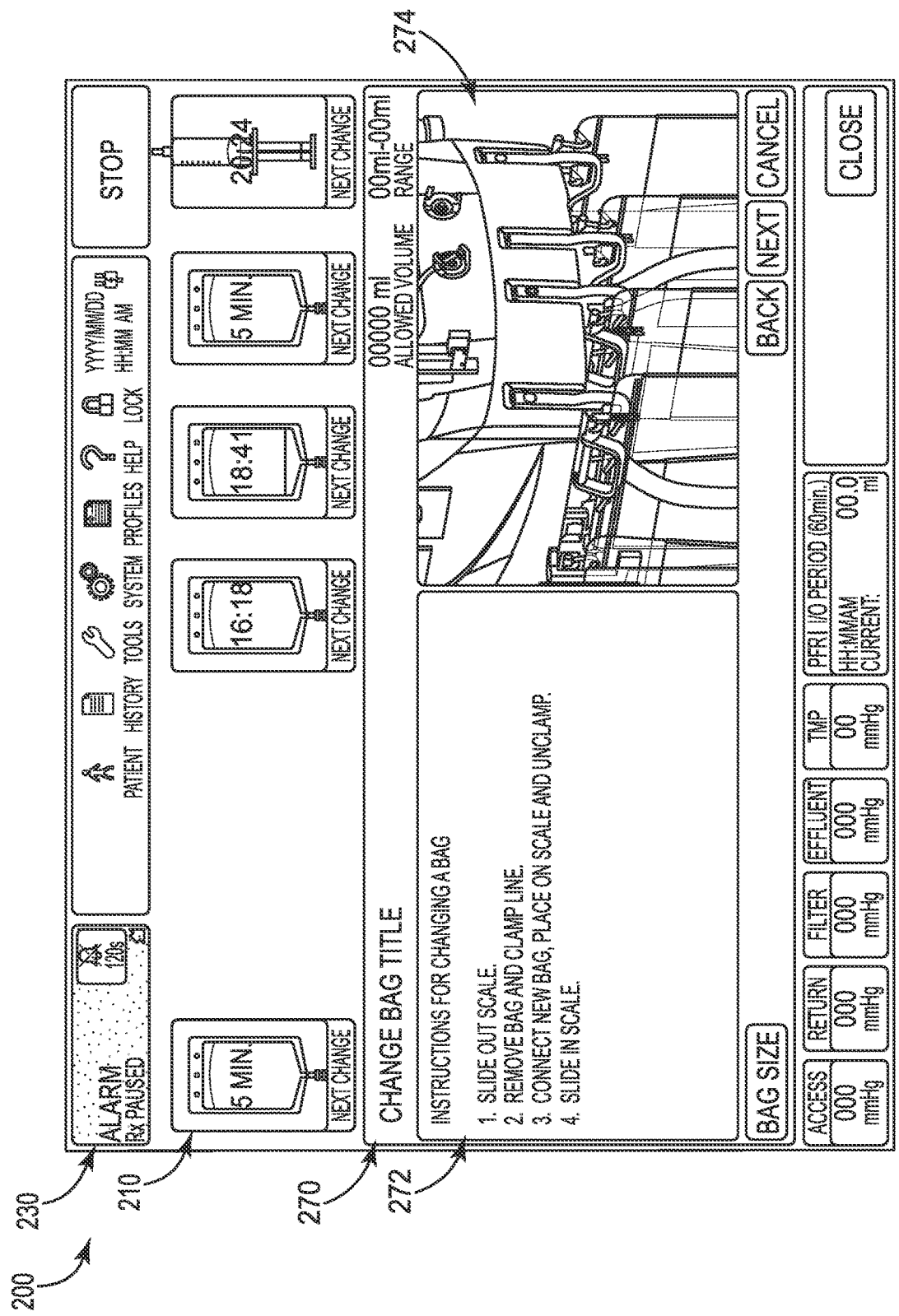

At least one of the action areas 260, such as action area 265 may be selected by an operator to display an instruction region 270 as shown in FIG. 8. The instruction region 270 may include information relevant to curing the issued alarm. For example, the instruction region 270 may include text 272 and graphics 274 that may instruct an operator how to fix the issued alarm. As shown, four steps are described in the text 272 of the instruction region 270. The graphic 274 may change for each step and may graphically depict the action to be performed for each step. For example, as shown, the step "Slide out scale" is highlighted, and as such, the graphic 274 may depict the scale being slid out.

The action areas 260 may include a "More Info" action area 263 that when selected by an operator may be configured to display an information region that may include more information regarding the issued alarm than the information area 254 of the alarm region 250. The action areas 260 may further include one or more ways, or processes, for curing an issued alarm, for temporarily curing an issued alarm, for providing one or more actions to be performed within the alarm state (e.g., processes and actions for raising or lowering a syringe, etc.), for providing override buttons/areas to temporarily raise or lower an alarm limit, for completely overriding an issued alarm, etc.

An operator may want to mute (e.g., temporarily override, postpone, quiet, etc.) the issued alarm such that, e.g., the operator may fix, or cure, the alarm without being repeatedly reminded of the alarm, etc. To provide the functionality to mute the issued alarm, the alarm region 250 may include a mute area 280 that may be selectable by an operator to "mute" the issued alarm for a selected period of time. As shown, the mute area 280 is graphically depicted as a depressible button with an icon of a bell 282 making sounds (e.g., sound "waves" emanating from the bell). When an operator selects the mute area 280, one or more indications such as, e.g., sounds from the exemplary system, blinking lights on the exemplary system (e.g., located on top of the system, etc.), flashing colors on the graphical user interface 200, etc. may be stopped (e.g., silenced, muted, turned off, restricted, etc.) for a selected period of time.

The selected period of time may be configured or preselected to be between about 30 seconds and about 360 seconds. For example, the selected period of time may be greater than or equal to about 30 seconds, greater than or equal to about 45 seconds, greater than or equal to about 60 seconds, greater than or equal to about 90 seconds, greater than or equal to about 120 seconds, greater than or equal to about 180 seconds, greater than or equal to about 240 seconds, etc. Further, for example, the selected period of time may be less than or equal to about 360 seconds, less than or equal to about 300 seconds, less than or equal to about 240 seconds, less than or equal to about 180 seconds, less than or equal to about 120 seconds, less than or equal to about 90 seconds, less than or equal to about 60 seconds, etc.

Figure 5:
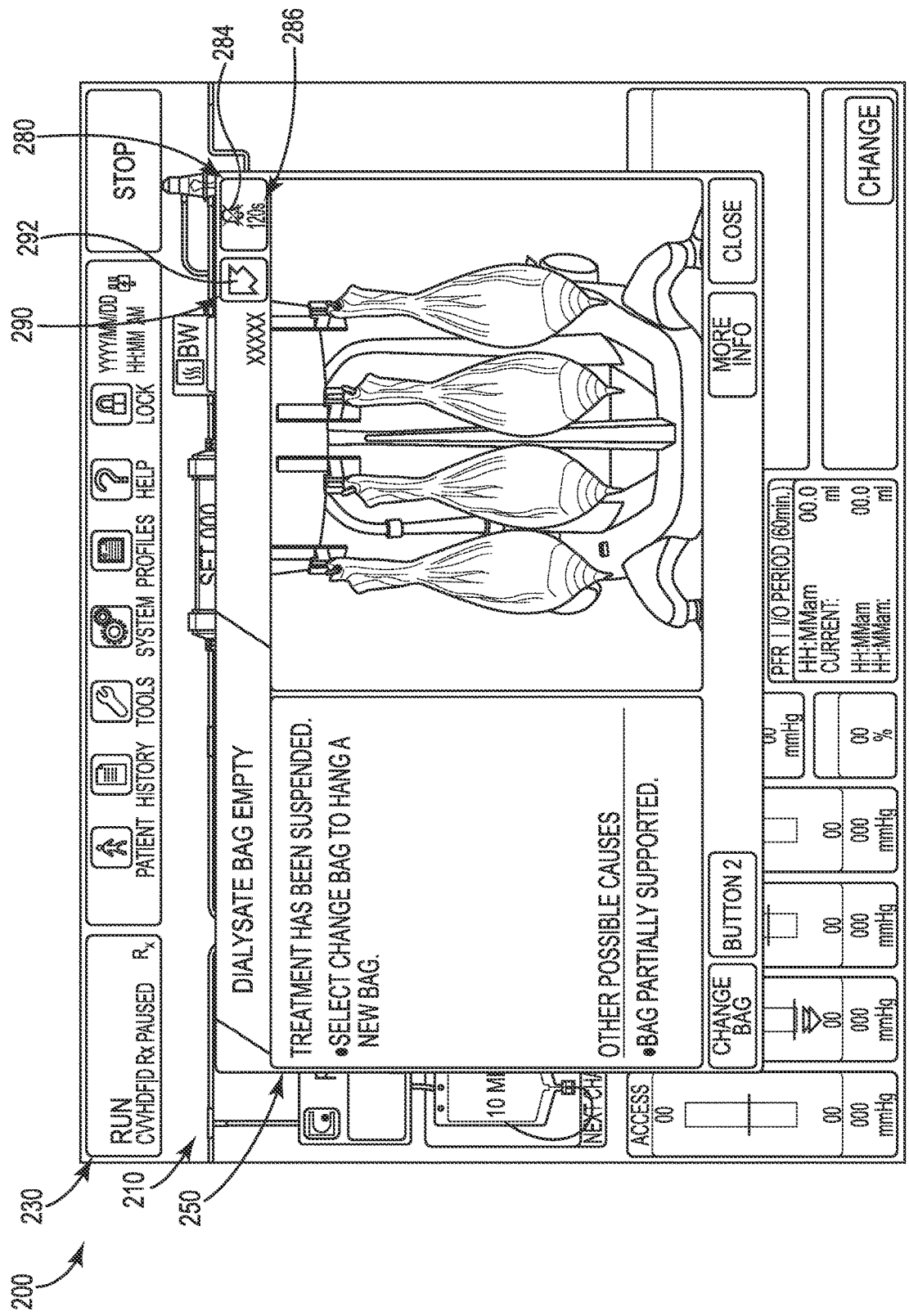

After an operator has selected the mute area 280 to "mute" the issued alarm, the graphics depicted in the mute area 280 may change to indicate that the alarm has been muted as shown in FIG. 5. For example, as shown, the solid bell graphic 282 has been changed into an outline of a bell 284, an "X" has been depicted over the outlined bell, and the sound "waves" emanating from the bell have been removed. Additionally, an alphanumerical representation (e.g., "120 s" represents 120 seconds) of an amount of time left 286 in the selected time period may be depicted in the mute area 280. The amount of time left 286 may decrement, decrease, or "count down" to zero (e.g., when the selected time period has "run out of time") when, or at which time, the alarm will be "un-muted." When the alarm is "un-muted," the one or more indications such as, e.g., sounds, blinking lights, flashing colors on the graphical user interface 200, etc. may be re-started (e.g., initiated, commenced, turned on, etc.).

The alarm region 250 may be configured to be docked (e.g., moved, minimized, shrunk, relocated, etc.) to another region or area of the graphical user interface 200. In one or more embodiments, the region of the graphical user interface 200 that the alarm region 250 may be docked to may be referred to generally as the dock region. The dock region may be any one of the many regions depicted on the graphical user interface 200. Further, the alarm region 250 may be depicted on any of the many regions of the graphical user interface 200 when the alarm is issued.

In the embodiments described herein, the region of the graphical user interface 200 within which the alarm region 250 may be docked, e.g., the dock region, may be smaller, or substantially smaller, than the region of the graphical user interface 200 within which the alarm region 250 originates (e.g., displayed originally when the alarm is issued). Conversely, the region of the graphical user interface 200 within which the alarm region 250 originates (e.g., displayed originally when the alarm is issued) may be larger, or substantially larger, than the region of the graphical user interface 200 within which the alarm region 250 may be docked, e.g., the dock region. In the embodiments described herein, the alarm region 250 is originally displayed in the operations region 210 and is dockable to the status region 230, and thus, the operations region 210 and the status region 230 will be used herein to describe exemplary size relationships between the region where the alarm region 250 originates and the region where the alarm region 250 may be docked. For example, the status region 230 may be less than one half of the size of the operations region 210, the status region 230 may be less than one quarter of the size of the operations region 210, the status region 230 may be less than one eighth of the size of the operations region 210, and the status region 230 may be less than one tenth of the size of the operations region 210. In other words, the status region 230 may be 50% or smaller than the operations region 210, the status region 230 may be 25% or smaller than the operations region 210, the status region 230 may be 12.5% or smaller than the operations region 210, and the status region 230 may be 10% or smaller than the operations region 210. Conversely, for example, the operations region 210 may be 10 times larger than the status region 230, the operations region 210 may be 8 times larger than the status region 230, the operations region 210 may be 4 times larger than the status region 230, and the operations region 210 may be 2 times larger than the status region 230. In other words, the operations region 210 may be 200% or larger than the status region 230, the operations region 210 may be 400% or larger than the status region 230, the operations region 210 may be 800% or larger than the status region 230, and the operations region 210 may be 1000% or larger than the status region 230.

In the embodiments described herein, the alarm region 250 may be displayed within the operations region 250, and the alarm region 250 from the operations region 210 may be configured to be docked to the status region 230 of the graphical user interface 200. It is to be understood that in other embodiments, that upon alarm issuance, the alarm region 250 may be displayed in, or within, regions of the graphical user interface 200 other than the operations region 210 and further, that the alarm region 250 may be docked to regions of the graphical user interface other than the status region 230. An operator may want to dock the alarm region 250 such that the operator may, e.g., view the entire operations region 210, view another portion of the operations region 210, modify one or more values or variables on the operations region 210, initiate, or select, other regions or areas of the graphical user interface 200 to perform various tasks or processes, adjust one or more settings, adjust one or more flow rates, change one or more reservoirs, view system, treatment, and/or patient history, review help information, adjust one or more components, etc. For example, when the alarm region 250 is docked, the operations region 210 may be enabled for interaction or functionality by an operator to, e.g., adjust one or more settings, etc. In at least one embodiment, the operations region 210 may be disabled for interaction by an operator even when the alarm region 250 is docked.

When the alarm region 250 is docked, the issued alarm is still active. In other words, docking the alarm region 250 from the operations region 210 does not cure, or fix, the issued alarm. Instead, the alarm region 250 may be merely moved to, or depicted in, a different location within the graphical user interface 200. An operator may dock the alarm region 250 by, e.g., selecting an area in the alarm region 250, touching and dragging the alarm region 250 to another region or area of the graphical user interface 200, swiping the alarm region 250 to another region or area of the graphical user interface 200, and/or performing any type of gesture on the graphical user interface 200.

Additionally, when the alarm region 250 is docked, the issued alarm may also be muted simultaneously. In other words, an operator may mute an issued alarm and dock the alarm region 250 in one step (e.g., by docking the alarm region 250). Further, if an operator opted to select an action area 260 to, e.g., address or cure the alarm, the selection of the action area 260 may also mute the alarm. In other words, an operator may simultaneously mute an issued alarm and initiate a process to cure, or address, the alarm in one step (e.g., selecting an action area 260).

As shown in FIG. 5, the alarm region 250 includes a dock area 290 that may be selectable (e.g., touched) by an operator to dock the alarm region 250 from the operations region 210 to a dock region such as, e.g., the status region 230. The dock area 290 is graphically depicted as a depressible button with an icon of an arrow 292 (e.g., pointing in the direction where the alarm region 250 may be docked).

Figure 6:
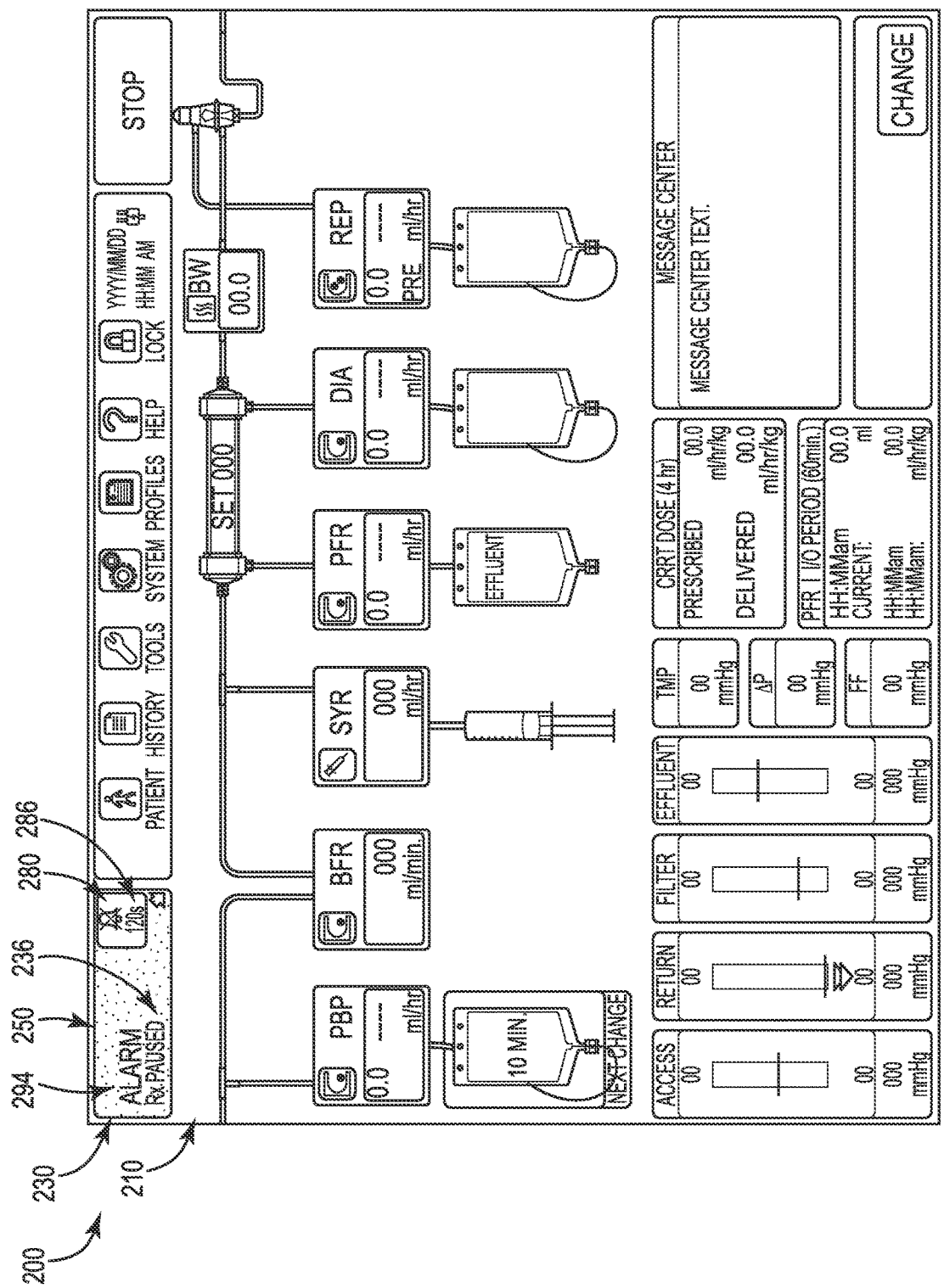

After the operator has selected the dock area 290, the alarm region 250 may be displayed within, appear within, or be relocated to, the status region 230 as shown in FIG. 6. Although the alarm region 250 is described herein as being "docked" in, or within, the status region 230, it is to be understood that all the graphical elements, information, and/or functionality of the alarm region 250 may not be actually (e.g., spatially, etc.) moved into the status region 230, but instead, the alarm region 250 as shown in FIGS. 4-5 may disappear, or be removed, revealing the operations region 210 (e.g., the entire operations region) while one or more graphical elements, information, and/or functionality of the alarm region 250 may be displayed within the status region 230 and one or more areas of the status region 230 may appear differently than the one or more areas had prior to the docking of the alarm region 250.

For example, when the alarm region 250 is docked, the graphical depiction of the status region 230 may change to indicate that the alarm region 250 is docked therein. Further, for example, prior to the docking, the status region 230 may be configured to display the machine status 232, the therapy type 234, and the therapy status 236 as shown in FIG. 3. After the docking, the therapy type 234 may be replaced by an alphanumeric string 294 describing the issued alarm. Although as shown in FIG. 6, the alphanumeric string 294 recites the word "Alarm," the alphanumeric string 294 may include any information related to the alarm such as, e.g., the type of alarm and/or the severity of the alarm. When the alarm region 250 is docked in the status region 230, the status region 230 may still display, or depict, one or more items or areas that the status region 230 had shown prior to the docking of the alarm region 250 such as the therapy status 236. Further, when the alarm region 250 is docked in the status region 230, the mute area 280 may also be depicted in the status region 230 and may provide all the same functionality as the mute area 280 when the alarm region 250 was not docked. Additionally, the status region 230 may change color and/or provide any other visual indication to indicate that an alarm region 250 is docked therein.

Figure 7:
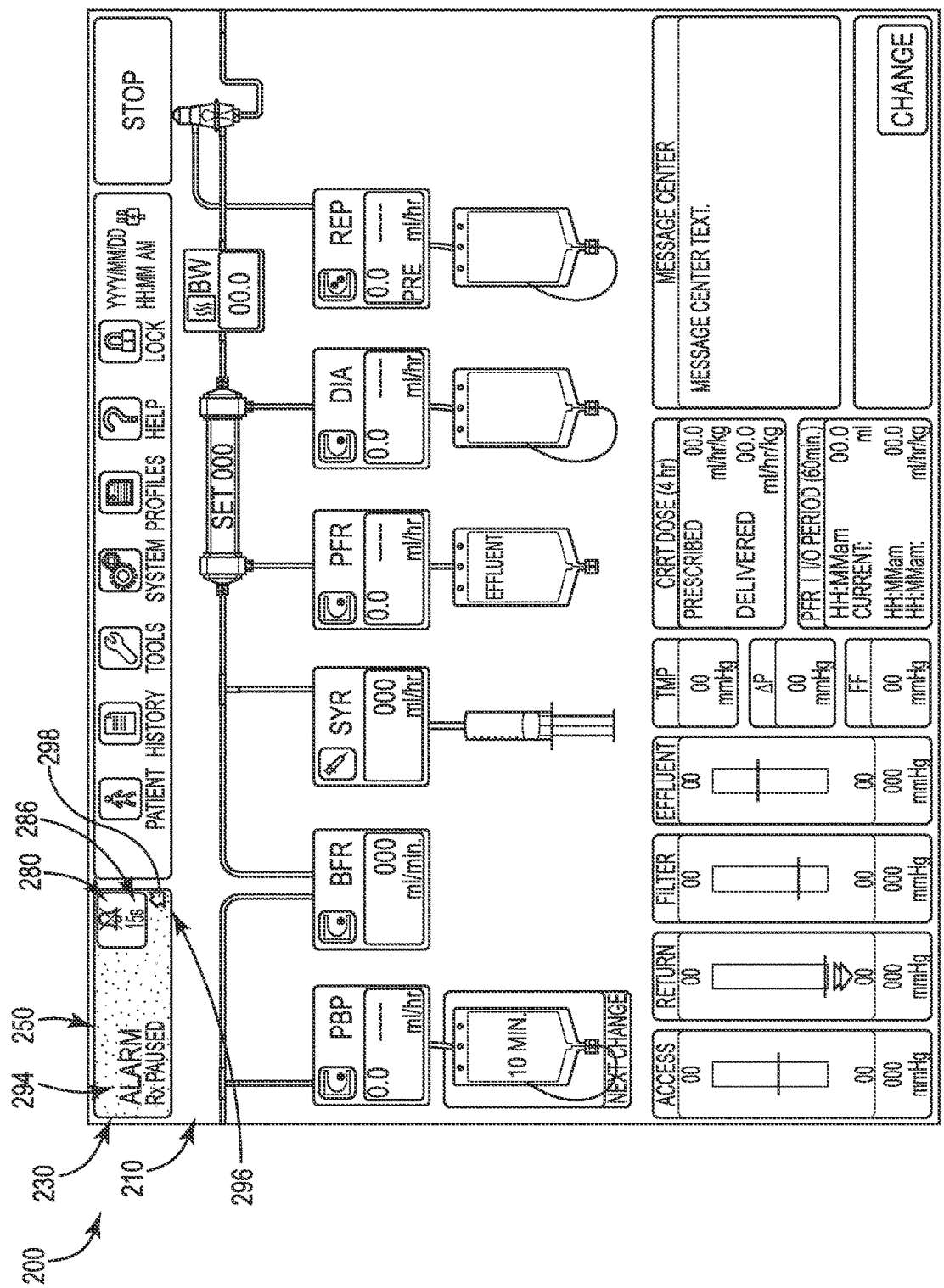

As described herein, the mute area 280 shown in the status region 230 when the alarm region 250 is docked into the status region 230 may display the same information and provide the same functionality as when the mute area 280 was shown in the "undocked" alarm region 250 depicted in FIGS. 4-5. For example, the amount of time left 286 in the selected time period may be depicted in the mute area 280 and may decrement, decrease, or "count down" to zero. As shown in FIG. 6, the amount of time left 286 is 120 seconds, and as shown in FIG. 7, the amount of time left 286 has decremented to 15 seconds. Thus, in FIG. 7, the issued alarm may be "un-muted" in 15 seconds unless, e.g., an operator cures, or fixes, the alarm, an operator "re-mutes" the alarm by selecting the mute area 280, etc. Further, an issued alarm may be "re-muted" prior the expiration of the selected time period.

A operator may "un-dock" the alarm region 250 from the status region 230 by, e.g., selecting an area in the alarm region 250, touching the status region 230 and dragging the alarm region 250 to another region or area of the graphical user interface 200, swiping the status region 230 to another region or area of the graphical user interface 200, and/or performing any type of gesture on the graphical user interface 200. As shown, the status region 230 may further depict an undock area 296 that may be selectable by an operator to "un-dock" (e.g., move, relocate, etc.) the alarm region 250 from the status region 230 to another region or area of the graphical user interface 200. As shown, the undock area 296 depicts an icon of an arrow 298 pointing in the direction that the alarm region 250 may be undocked (e.g., moved) to.

More than one alarm region 250 may be docked into the status region 230 at the same time. When more than one alarm region 250 is docked into the status region 230 at the same time, the status region 230 may provide one or more indications that two or more alarm regions 250 are docked. For example, a number may be displayed within the status region 230 that indicates the number of alarm regions 250 docked therein. Further, graphical elements such as dots (e.g., a row of dots, each dot indicating an alarm region 250) may be displayed within the status region 230 to indicate the number of alarm regions 250 docked therein. Further, when an operator selects the status region 230 when more than one alarm region 250 is docked therein, a list, or other graphical representation, of all the alarm regions 250 may be presented to allow the operator to select the alarm region 250 to "undock." Additionally, an operator may also be able to undock more than one alarm region 250 from the status region 230 at the same time (e.g., selecting the status region 230 and/or the undock area 296 may undock all alarm regions 250, etc.).

Figure 9:
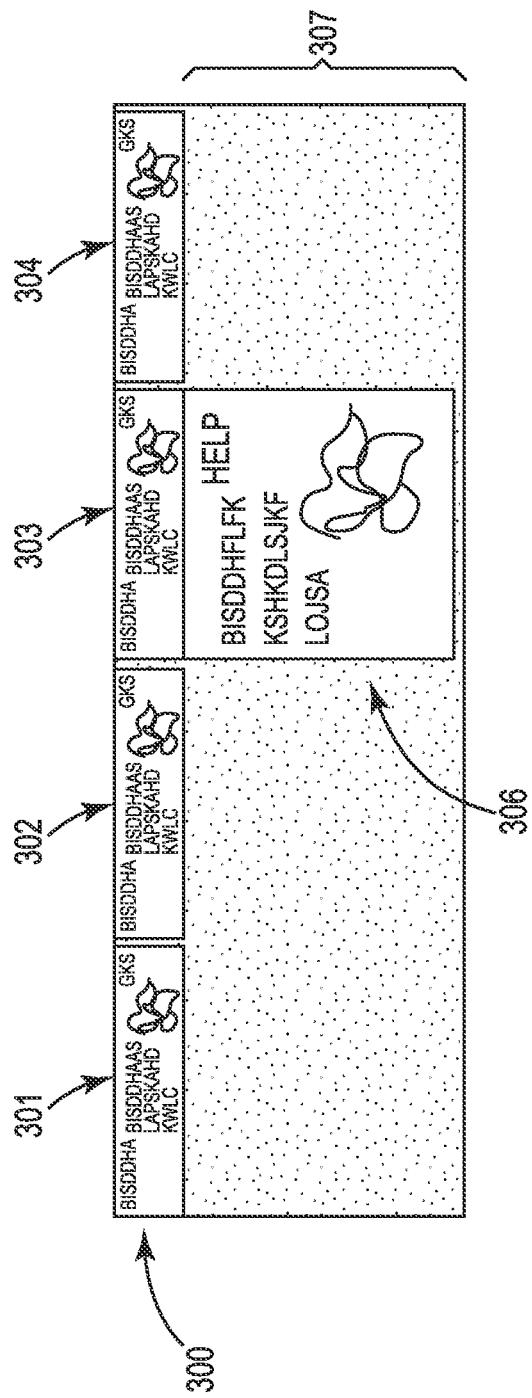
FIG. 9 shows a dock region of a graphical user interface related to alarms for use in extracorporeal blood treatment systems, for example, such as shown generally in FIGS. 1-2.

Further, as shown in FIG. 9, when more than one alarm region 250 is docked, all of the docked alarms (or just two or more of the docked alarms) may be presented in a docked to do list manner (e.g., displayed simultaneously such as in separate dock areas as shown in FIG. 9, displayed in stacked manner, etc.). For example, each of the docked alarms may be displayed as a separate dock alarm area 301-304 within a larger dock region 300 (e.g., the status region 230). Such docked alarms may be arranged either by the user or automatically within the dock region 300. For example, such an arrangement may be based on priority of the alarms. Further, for example, the docked alarms may be coded to identify to the user the priority of the alarms, to identify one of the docked alarms that needs to be handled first (e.g., docked alarm area 303 is of a different color to identify its priority and/or to identify it as the alarm that needs attention first before the other alarms), to illustrate the type of alarm, etc. Still further, information areas, such as information area 306 in information region 307, may be associated with each of the docked alarm areas and/or just the alarm area having the highest priority to provide additional information to the user for correcting the alarm or providing any other assistance in handling the multiple alarms. Such additional information may be provided in the form of a pull-down area from the alarm being highlighted, may be presented as a pop-up area, etc.

Additionally, one or more animations may be depicted by the exemplary graphical user interface when docking or un-docking the alarm region 250 to, e.g., provide spatial awareness (e.g., to prevent disorientation) and/or alarm awareness (e.g., that the issued alarm has not been cured) to an operator regarding the present location of the alarm region 250. For example, when docking the alarm region 250 from the operations region 210 to the status region 230, the alarm region 250 may be depicted as moving from the center of the graphical user interface 200 to the status region 230 while simultaneously shrinking to "fit" within the status region 230. Thus, an operator may interpret such animations to show that the alarm region 250 has been moved and shrunk to fit within the status region 230 (e.g., the operator still is aware that the alarm is present or ongoing). Conversely, when the alarm region 250 is un-docked from the status region 230, the alarm region 250 may be depicted as moving from the status region 230 to the center of the graphical user interface 200 while simultaneously growing to include all of the information and/or functionality of the alarm region 250 depicted in FIGS. 3-4. Thus, an operator may interpret such animations to show that the alarm region 250 has been moved from the status region 230 to its undocked location (e.g., within the operations region 210) and expanded to, or back to, its undocked size.

Further, for example, when docking the alarm region 250 from the operations region 210 to the status region 230, an arrow may be temporarily depicted between the operations region 210 to the status region 230 (e.g., pointing at the status region 230 from the operations region 210). Likewise, when undocking the alarm region 250 from the status region 230 to the operations region 210, an arrow may be temporarily depicted between the status region 230 to the operations region 210 (e.g., pointing at the operations regions 210 from the status region 230).

The alarm region 250 may be further configured to automatically un-dock when the selected time period for the muted alarm expires. For example, as shown in FIG. 7, if an operator does not cure or re-mute the alarm before the selected time period expires (e.g., in the next 15 seconds), the alarm region 250 may automatically un-dock from the status region 230 to the operations region 210.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the systems and methods described herein. Various modifications of the illustrative embodiments, as well as additional embodiments of the disclosure, will be apparent upon reference to this description.

What is claimed is:
1. An extracorporeal blood treatment system comprising:
a display apparatus comprising a graphical user interface, wherein the graphical user interface is configured to depict an operations region; and a computing apparatus comprising one or more processors operatively coupled to the display apparatus, wherein the computing apparatus is configured to:
display on the graphical user interface the operations region;
issue an alarm indicating an issue with an extracorporeal blood treatment being performed;
display, when an alarm is issued, an alarm region in the operations region, wherein the alarm region comprises information relevant to the issued alarm; and
allow a user to dock the alarm region to another region of the graphical user interface other than the operations region.

2. A method for an extracorporeal blood treatment system comprising:
providing a graphical user interface configured to depict an operations region;
displaying on the graphical user interface the operations region;
issuing an alarm indicating an issue with an extracorporeal blood treatment being performed;
displaying, when an alarm is issued, an alarm region in the operations region, wherein the alarm region comprises information relevant to the issued alarm; and
allowing a user to dock the alarm region to another region of the graphical user interface other than the operations region.

3. The system of claim 1, wherein a status region is further displayed on the graphical user interface, and wherein the alarm region is docked to the status region.

4. The system of claim 3, wherein the operations region is larger than the status region.

5. An extracorporeal blood treatment system comprising:
a display apparatus comprising a graphical user interface, wherein the graphical user interface is configured to depict a dock region; and
a computing apparatus comprising one or more processors operatively coupled to the display apparatus, wherein the computing apparatus is configured to:
display on the graphical user interface the dock region;
issue an alarm indicating an issue with an extracorporeal blood treatment being performed;
display, when an alarm is issued, an alarm region on the graphical user interface, wherein the alarm region comprises information relevant to the issued alarm; and
allow a user to dock the alarm region to the dock region.

6. A method for an extracorporeal blood treatment system comprising:
providing a graphical user interface configured to depict a dock region;
displaying on the graphical user interface the dock region;
issuing an alarm indicating an issue with an extracorporeal blood treatment being performed;
displaying, when an alarm is issued, an alarm region on the graphical user interface, wherein the alarm region comprises information relevant to the issued alarm; and
allowing a user to dock the alarm region to the dock region.

7. The system of claim 1, wherein the alarm region further comprises a dock area configured to be selected by a user to dock the alarm region.

8. The system of claim 1, wherein animation is used to show the alarm region moving and shrinking as the alarm region is being docked.

9. The system of claim 1, wherein the alarm region further comprises a mute area configured to be selected by a user to mute the alarm.

10. The system of claim 1, wherein the alarm is muted automatically when the alarm is docked.

11. The system of claim 9, wherein the alarm region is further configured to depict an amount of time remaining prior to un-muting the alarm after being muted.

12. The system of claim 11, wherein the mute area is selectable by a user to reset the amount of time remaining prior to un-muting the alarm.

13. The system of claim 1, wherein the computing apparatus is further configured to execute allowing, when the alarm region is docked, a user to undock the alarm region.

14. The system of claim 1, wherein the docked alarm region further comprises an undock area configured to be selected by a user to undock the alarm region.

15. The system of claim 1, wherein the alarm region further comprises at least one action area, wherein the computing apparatus is further configured to execute displaying on the graphical user interface, when an action area of the at least one action area is selected, an instruction region comprising information relevant to curing the issued alarm.

16. The system of claim 1, wherein the alarm region further comprises at least one action area, wherein the computing apparatus is further configured to execute displaying on the graphical user interface, when an action area of the at least one action area is selected, more information relevant to the issued alarm.

17. The system of claim 1, wherein an operations region is displayed on the graphical user interface, wherein the operations region comprises a plurality of fluid areas, wherein each fluid area of the plurality of fluid areas depicts a flow rate, and further wherein, when an alarm is issued, the alarm region is depicted at least partially over the plurality of fluid areas.

18. The system of claim 1, wherein the computing apparatus is further configured to execute disabling, when the alarm region is displayed on the graphical user interface without being docked, a user from interacting with any portion the graphical user interface except the alarm region.

19. The system of claim 1, wherein the computing apparatus is further configured to execute, allowing, when the alarm region is docked, a user to interact with the graphical user interface.

20. The system of claim 1, wherein the computing apparatus is further configured to execute removing, when the alarm is cured, the alarm region from the graphical user interface.

21. The system of claim 1, wherein the size of the alarm region is scaled based on a severity of the issued alarm or a status light may be activated in a mode corresponding to the alarm.

22. The system of claim 1, wherein a status region is further displayed on the graphical user interface, wherein the status region comprises therapy information relevant to the extracorporeal blood treatment being performed, wherein the alarm region is docked to the status region, and wherein, when the alarm region is docked in the status region, the alarm region comprises at least a portion of the therapy information of the status region.

23. The system of claim 1, wherein a dock region is displayed on the graphical user interface, wherein a plurality of alarm regions are docked and displayed in one or more alarm dock areas of the dock region.

* * * * *